(12) United States Patent
Bednar et al.

(10) Patent No.: US 10,444,212 B2
(45) Date of Patent: Oct. 15, 2019

(54) METHOD FOR DETERMINING THE CONCENTRATION OF GLUCORAPHANIN AND/OR SULFORAPHANE IN A PLANT

(71) Applicants: QFOOD GMBH, Gundelfingen (DE); SMAAKMAKER HOLDING B.V., Enkhuizen (NL)

(72) Inventors: Sonja Bednar, Gundelfingen (DE); Holger Klapproth, Freiburg (DE); Robert Seidel, Freiburg (DE)

(73) Assignees: QFOOD GMBH, Gundelfingen (DE); SMAAK MAKER HOLDING B.V., Enkhuizen (NL)

( * ) Notice: Subject to any disclaimer, the term of this patent is extended or adjusted under 35 U.S.C. 154(b) by 413 days.

(21) Appl. No.: 15/441,307

(22) Filed: Feb. 24, 2017

(65) Prior Publication Data
US 2017/0205384 A1    Jul. 20, 2017

Related U.S. Application Data

(63) Continuation-in-part of application No. PCT/EP2015/001652, filed on Aug. 11, 2015.

(30) Foreign Application Priority Data

Aug. 25, 2014  (DE) .................. 10 2014 012 367

(51) Int. Cl.
| | | |
|---|---|---|
| *A61K 36/31* | (2006.01) | |
| *G01N 33/00* | (2006.01) | |
| *G01N 21/33* | (2006.01) | |
| *G01N 33/02* | (2006.01) | |
| *C12Q 1/00* | (2006.01) | |
| *G01N 33/487* | (2006.01) | |

(52) U.S. Cl.
CPC ......... *G01N 33/0098* (2013.01); *A61K 36/31* (2013.01); *C12Q 1/00* (2013.01); *G01N 21/33* (2013.01); *G01N 33/025* (2013.01); *G01N 33/487* (2013.01); *G01N 2201/12* (2013.01)

(58) Field of Classification Search
CPC .............. G01N 21/33; G01N 2201/12; G01N 33/0098; G01N 33/025; G01N 33/487; C12Q 1/00
See application file for complete search history.

(56) References Cited

U.S. PATENT DOCUMENTS

| | | | | |
|---|---|---|---|---|
| 5,725,895 A | * | 3/1998 | Fahey | A21D 2/36 426/49 |
| 6,242,018 B1 | * | 6/2001 | Fahey | A61K 36/00 426/425 |
| 8,927,007 B2 | * | 1/2015 | Talalay | A61K 38/47 424/450 |
| 9,433,654 B2 | * | 9/2016 | Efstathiou | A61K 36/31 |
| 2008/0312164 A1 | * | 12/2008 | Rajski | C07D 231/26 514/24 |
| 2009/0081138 A1 | * | 3/2009 | Ashurst | A61K 36/31 424/59 |
| 2010/0317518 A1 | * | 12/2010 | Stevens | A01N 51/00 504/117 |
| 2015/0209395 A1 | * | 7/2015 | Raskin | A61K 36/185 424/776 |
| 2016/0243176 A1 | * | 8/2016 | Raskin | A61K 36/185 |
| 2018/0332881 A1 | * | 11/2018 | Lambers | A23L 33/40 |

OTHER PUBLICATIONS

Soni, K; Kohli, K "Broccoli sulforaphane: an insight into the analytical aspect and ultraviolet spectroscopic method development and validation" World Journal of (Year: 2015).*
Budnowski,J; Hanschen,FS; Lehmann,C; Haack,M; Brigelius-Flohe, R; Kroh, LW; Blaut, M; Rohn, S; Hanske, L "A derivatization method for the simultaneous detection of glucosinolates and isothiocyanates in biological samples" Analytical Biochemistry, 2013, 441(2), 199-207; doi:10.1016/j.ab.2013.07.002. (Year: 2013).*

* cited by examiner

*Primary Examiner* — Aaron J Kosar
(74) *Attorney, Agent, or Firm* — Klaus J. Bach

(57) ABSTRACT

In a method for determining the concentration of glucoraphanin in a plant a sample of the plant is contacted by a polar uncharged organic solvent and comminuted such that glucoraphanin and plant material contained in the sample are dissolved in the solvent and, after removal of undissolved plant parts, the extract formed thereby is subjected to an UV-absorption measurement wherein for a first wavelength range of 200-270 nm, an absorption signal is recorded. A second derivative of the absorption signal is then obtained for a second wavelength range of 240-250 nm and the value of the minimum of the second derivative is determined and, based on this value, a concentration value for the glucoraphanin in the plant is established.

12 Claims, 2 Drawing Sheets

METHOD FOR DETERMINING THE CONCENTRATION OF GLUCORAPHANIN AND/OR SULFORAPHANE IN A PLANT

This is a continuation in part application of pending international patent application PCT/EP2015/001652 filed Aug. 11, 2015 and claiming the priority of German patent application 10 2014 012 367.7 filed Aug. 25, 2014.

BACKGROUND OF THE INVENTION

The invention resides in a method for determining the concentration of glucoraphanin in a plant wherein:
a) a sample of the plant is provided,
b) the sample is contacted by a polar non-charged organic solvent and so comminuted that glucoraphanin and further plant material contained in the sample is dissolved in the solvent and
c) from the extract obtained in this way plant parts are removed to clear the extract.

Further, the invention concerns a method for determining the concentration of bio-available sulforaphane in a plant wherein the plant contains glucoraphanin and a splitting enzyme which is spatially separated therefrom and wherein the plant forms sulforaphane when the splitting enzyme comes into contact with the glucoraphanin.

Such a method for determining the concentration of glucoraphanin is known in practice. Herein, a sample of plant to be examined is provided and is comminuted in an acetone-containing solvent in such a way that glucoraphanin contained in the sample is dissolved in the solvent. Subsequently, the extract obtained thereby is first cleared and cleaned. Then a liquid chromatography is performed wherein the extract is moved under high pressure through a column. Along the column various molecules contained in the extract are separated from one another. The column is irradiated by UV light which is absorbed by the molecules. The presence of the glucoraphanin molecules at a predetermined location of the column is detected by an optical sensor which is sensitive in the UV range. The glucoraphanin molecules are then quantified in a further method step by mass spectrometry.

The known method is used in particular for the examination of broccoli cress or respectively broccoli sprouts. Broccoli cress has a high content of glucoraphanin and also contains a splitting enzyme which is spatially separated from the glucoraphanin and which comes into contact with the glucoraphanin when the plant is damaged. Hereby the glucoraphanin is split into sulforaphane and a sugar rest. Basically, the sulforaphane serves to keep pests away from the plant. Examinations have shown that foods which contain sulforaphane in a sufficient concentration are also helpful for the human health. Therefore broccoli cress is used preferably for medical studies. In order to ensure that studies are comparable, the concentration of the glucoraphamine and, in particular, the concentration of the bio-available sulforaphane present in the broccoli cress must be known accurately. Herein the concentration of the bio-available sulforaphane is understood to be the concentration of the sulforaphane which can be formed by the plant itself when the glucoraphanin contained in the plant comes into contact with the splitting enzyme which is also contained in the plant.

The known method of determining the concentration of the glucoraphanin has the disadvantage that its performance is complicated and time-consuming and that large apparatus are required which are generally present only in a suitably equipped laboratory. It is a further disadvantage that the required analysis apparatus require maintenance and also require qualified personal for performing the testing. A method for determining the concentration of bio-available sulforaphane of the type mentioned earlier is not known as far as the applicant knows.

It is therefore the object of the present invention to provide a method of the type described above, whereby the concentration of glucoraphanin in a plant can be determined in a simple manner. A further object of the invention is to provide a method which facilitates a simple determination of the concentration of bio-available sulforaphane in a plant.

SUMMARY OF THE INVENTION

The invention comprises the following method steps:
a) a sample of the plant is provided,
b) the sample is contacted by a polar non-charged organic solvent and is so comminuted that glucoraphanin and further plant material contained in the sample are dissolved in the solvent,
c) from the extract obtained in this way unsolved plant components are removed so as to clear up the extract,
d) the cleared extract which contains glucoraphanin and further plant material is subjected to a UV-absorption examination wherein, for a first wavelength range of between 20 nm and 270 nm, an absorption measurement signal is recorded,
e) the second derivative of the Absorption measurement signal for a second wavelength range of 240 nm and 250 nm is formed, and
f) the value of the minimum of the second derivative in the second wavelength range is determined and from this value a concentration value for the concentration of the glucoraphanin is determined.

Surprisingly, by forming the second derivative of the absorption measurement signal, it is possible to compensate for the influence of the plant material dissolved in the solvent on the measuring result. In this way, it is possible to perform with the extract directly a UV absorption measurement without the need for cleaning the extract. The method according to the invention can be performed with an inexpensive hand-held apparatus in a simple manner. It is even possible to perform a test at the location of the plants to be examined in the field or on in a greenhouse. And since the method according to the invention can easily be automated, the testing can be performed reliably and rapidly by persons who do not need to have special qualifications.

In an advantageous embodiment of the invention, the absorption measurement signal is filtered by category and the second derivative is formed from the category-filtered absorption signal. With the category-filtering which may include a deep-pass filtering, background noise and similar nuisances can be suppressed so that they do not or not essentially affect the measurement accuracy. As smoothing filter for example a Savitzky-Golay filter may be used.

In a preferred further development of the invention, the plant contains, in addition to the glucoraphanin, a splitting enzyme which is spatially separated from the glucoraphanin and where, upon contact with the glucoraphanin, a sulforaphane is formed by the plant wherein:
a) a first sample of the plant is provided and, with the features of claim 1, a first concentration value for the concentration of the glucoraphanin in the first sample is determined,
b) a second example of the plant is provided, c) the second sample is comminuted so that the glucoraphanin comes into contact with the splitting enzyme, d) after a predetermined waiting time in which the sulforaphane is formed and evaporated in the second sample, e) the second sample is brought into contact with a polar uncharged organic solvent whereby the glucoraphanin and additional plant material contained in the second sample are dissolved in the solvent, f) for the second sample, the features f) of claim 1 are performed and g) the difference of the concentration value determined for the first sample and the concentration value determined for the second sample is determined as concentration value for the concentration of the bio-available sulforaphane of the plant.

Consequently, at least two tests are performed wherein, for at least a first test, the sample is brought into contact with the solvent immediately after it is taken from the plant so that the glucoraphanin is not or only shortly in contact with the splitting enzyme and no or only a small part of the glucoraphanin is split into sulforaphane and a sugar rest and is evaporated. Further, at least a second test is performed in which the sample is comminuted immediately after it is taken from the plant so that glucoraphanin contained in the sample comes into contact with the splitting enzyme. Except for the splitting enzyme already contained in the plant no splitting enzyme is added. After the sulforaphane has evaporated the sample is contacted by the solvent so that then only the part of the glucoraphanin which was originally in the sample is dissolved in the solvent which was not produced by the splitting enzyme into sulforaphane and the sugar rest and which was evaporated.

In the first and second tests, in each case, the concentration of the glucoraphanin is measured and from the concentration values obtained the difference is determined. This difference corresponds to the concentration of the glucoraphanin from which, by contact with the splitting enzyme contained in the sample, sulforaphane can be formed that is the concentration of the bio-available sulforaphane of the plant.

In a preferred embodiment of the invention, the absorption measurement signal obtained in step d) of claim 1 and for the step f) of claim 1 is compared with a limit value wherein, in case the absorption measurement signal exceeds the limit value, the extract is diluted in accordance with a dilution factor and the step d) of claim 1 is repeated with the diluted extract. The dilution factor is so selected that the absorption measuring signal of the diluted extract does not exceed the limit value. The steps e) and f) of claim 1 are then performed with the absorption measurement signal of the diluted extract and the dilution factor is taken into consideration in the determination of the concentration of the glucoraphanin in the plant. The limit value is preferably so selected that the measurement signal obtained with the absorption measurement is smaller than the value with which the absorption measurement reaches the area of the limit value. The limit value is preferably between 2 and 3.

The earlier mentioned object regarding the determination of the concentration of the bio-available sulforaphane can also be achieved with the features of claim 6, which provides for the following steps:

a) A first example of the plant is provided, b) the first sample is brought into contact with a polar non-charged organic solvent and comminuted such that the glucoraphanin contained in the sample and further plant material contained in the sample are dissolved in the solvent.

c) from the extract obtained in this way undissolved plant parts are removed to form the first extract, d) a second sample of the plant is then provided, e) the second sample is comminuted such that the second sample comes into contact with the splitting enzyme f) there is a waiting for a predetermined time selected so as to permit evaporation of the sulforaphane formed in the second sample, g) the second sample is contacted by a polar non-charged organic solvent so that glucoraphanin contained in the second sample and further plant material contained in the sample are dissolved in the solvent, h) from the second extract obtained in this way undissolved plant parts are removed so as to clear the extract, i) a first UV absorption measurement of the cleared first extract which includes the glucoraphamine and the further plant material is performed wherein for a first wavelength range between 200 nm and 270 nm a first absorption measurement signal is recorded, j) a second UV absorption measurement of the cleared second extract that contains the glucoraphanin and the further plant material is performed wherein for the first wavelength range a second absorption measurement is recorded, k) a differential signal is formed from the first absorption measurement signal and the second absorption measurement signal, l) a second derivative of the differential signal for a second wavelength range between 240 nm and 250 nm is formed, and m) the value of the minimum of the second derivative of the differential signal in the second wavelength range is determined and, depending on this value, a concentration value for the concentration of the sulforaphane is determined.

The concentration value for the concentration of the sulphoraphane available from the plant can therefore also be determined in that first the difference between absorption signals obtained in the first and the second test and then then the second derivative of the difference signal is formed, and, in the wavelength range from 240 nm and 250 nm, the value of the minimum of the second derivative is determined. Also with this method, with the extracts provides by the tests, the UV-absorption measurements can be performed directly without the need for cleaning the extracts. The method can be performed in a simple manner and can easily be automated.

In an advantageous embodiment of the invention the absorption measurement signal obtained in step i) of claim 6 is compared with a limit value, wherein, if the absorption measurement signal exceeds the limit value, the extract is diluted in accordance with a dilution factor and step i) of claim 6 is repeated with the diluted extract. The dilution factor is so selected that the absorption measurement signal of the diluted extract does not exceed the limit value. Then, in step k) of claim 6, as first absorption signal the absorption measurement signal of the diluted extract multiplied by the dilution factor is used. The limit value is preferably so selected that the measurement signal obtained during the absorption measurement is smaller than the value with which the absorption reaches the limit. Preferably, the limit value is between 2 and 3.

It is advantageous if the absorption measurement signal and/or the difference signal are smoothened by filtering and if the second derivative is formed from the smooth-filtered difference signal. By this smooth-filtering which may include deep-pass filtering, background noise and other disturbances can be depressed so that the measurement accuracy is not or essentially not detrimentally affected thereby.

In a preferred embodiment of the method, the plant is broccoli cress. This plant has a particularly high content of glucoraphanin and bio-available sulforaphane. As solvent, preferably methanol is used. This solvent can be disposed of after use without negative environmental effects.

Below an exemplary embodiment of the invention will be described in greater detail with reference to the accompanying drawings.

DESCRIPTION OF A PARTICULAR EMBODIMENT

In a method for determining the concentration of glucoraphanin in broccoli cress a first sample of the broccoli cress is provided which has a mass of 251 mg. The broccoli-cress contains glucoraphanin and a splitting enzyme which is spatially separated from the glucoraphanin but which is brought into contact therewith. Upon contact of the glucoraphanin with the splitting enzyme, sulforaphane is formed. The broccoli-cress furthermore includes additional plant material.

The first sample is mixed with a first amount of methanol which has a mass of 1760 mg and is comminuted to such an extent that the glucoraphanin contained in the first sample as well as further plant material is dissolved in the solvent. From the extract obtained in this way, undissolved plant parts are cleared out by filtering and/or centrifuging.

From the cleared extract 18 mg are taken and mixed with a second amount of methanol which has a mass of 759 mg, that is, the extract is diluted by a factor of 18/(18+795)=1: 43.2. The dilution factor is determined with the aid of an expectation value for the glucoraphanin concentration in such a way that an absorption measuring apparatus which is used during an absorption measurement performed in a further method step which will be described in greater detail, would be in an optimal measuring range when the concentration of glucoraphanin in the sample would coincide with the expected value.

Figure 1:
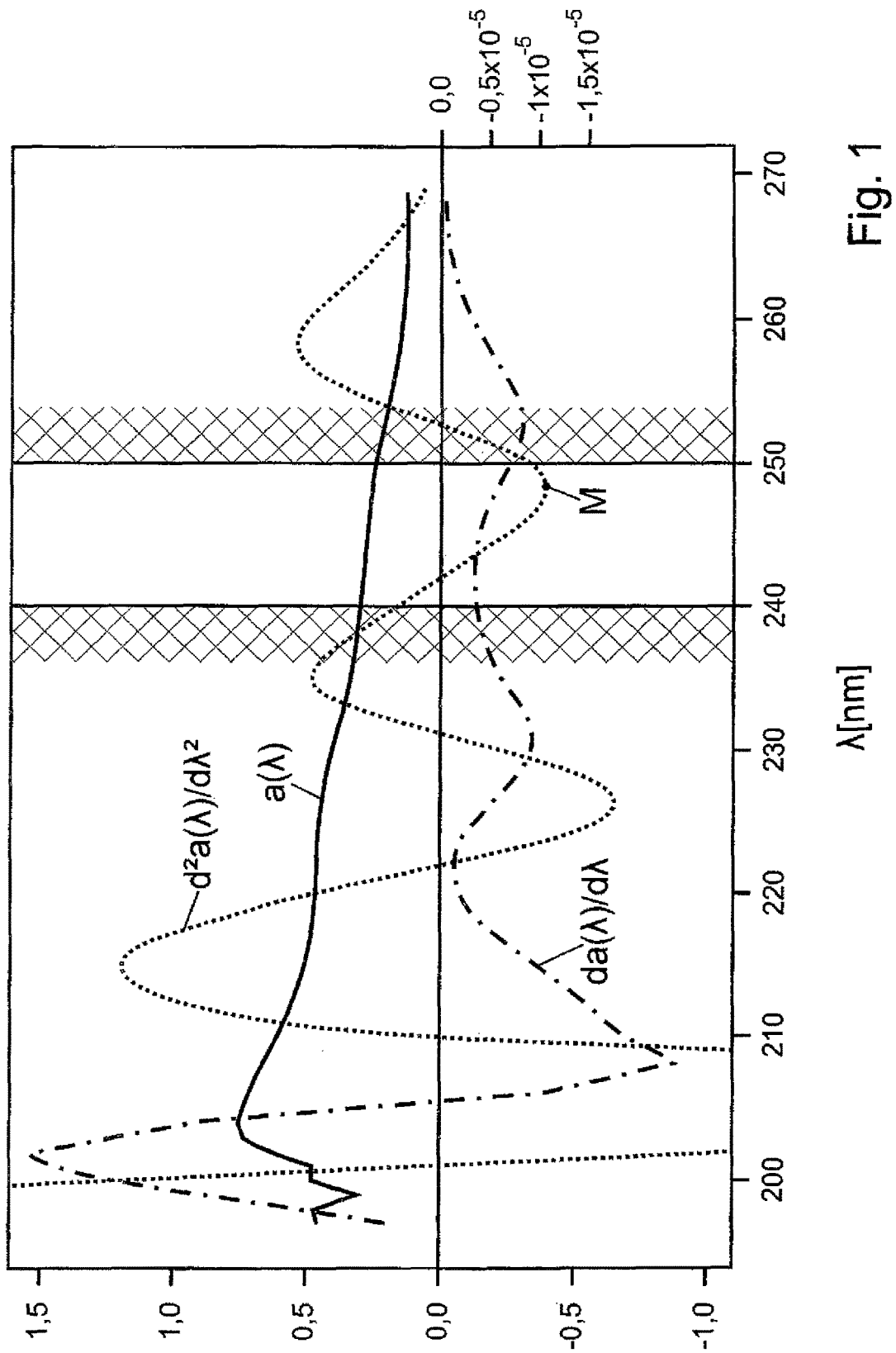
FIG. 1 shows a graphic representation of an absorption measurement signal $a(\lambda)$ as well as a first derivative $d^2a(\lambda)/d\lambda$ and its second derivative $d^2a(\lambda)/d\lambda^2$, wherein, on the base, the wavelength is indicated in nanometer (nm) and on the ordinate, at left, the adsorption or, respectively, the first derivative and, on the ordinate at right, the second derivative of the absorption are shown.

Now the already earlier mentioned UV absorption measurement of the cleaned diluted extract which contains the glucoraphanin and the additional plant material is performed. Herein, the absorption measurement signal $a(\lambda)$ is determined for a first wavelength range of 200 nm to 270 nm as shown in FIG. 1. The absorption measurement signal $a(\lambda)$ has a resolution of 0.2 nm. The absorption signal $a(\lambda)$ is smoothened by a Savitzky-Golay filter for example over 21 to 31 points of the spectral resolution.

If in the first wavelength range measurement the measured absorption spectrum has values above 2.5, it is assumed that the absorption measurement apparatus had reached saturation. In this case, the test is interrupted and a new first test is initiated in which a greater dilution factor is selected than in the first try. The method steps described above are than repeated for the new test.

If the absorption spectrum measured in the first wavelength range does not have measurement values above 2.5, the absorption measurement signal $a(\lambda)$ in a second wavelength range of 240 nm to 250 nm a mathematically second derivative is formed. The first derivative $da(\lambda)/d\lambda$ and the second derivative $d^2a(\lambda)/d\lambda^2$ are shown graphically in FIG. 1. They can be calculated numerically by a microcomputer. If necessary the second derivative can also be done together with the Savitzky-Golay smoothing in a single step.

In the second wavelength range (240 nm-250 nm), the value of the minimum M of the second derivative $d^2a(\lambda)/d\lambda^2$ of the absorption measurement signal $a(\lambda)$ is determined. As apparent from FIG. 1, the minimum M 1 is present at a wavelength $\lambda_M$ of about 248 nm and the value of the minimum M is $9.37\times10^5$. As apparent from FIG. 1, the absorption line of about 248 nm is in the absorption measurement signal $a(\lambda)$ not directly recognizable. Therefore the absorption measurement signal $a(\lambda)$ cannot be directly used for determining the concentration of the glucoraphanin concentration in the first sample.

The second derivative however shows a clear local minimum at the wavelength 246 nm followed by a local maximum which is in the wavelength range of 241 nm and 263 nm. The background spectrum which is to a large extent part of the spectrum becomes negligible with the second derivative and a focusing on a small range of the spectrum between 200 nm and 270 nm.

Figure 2:
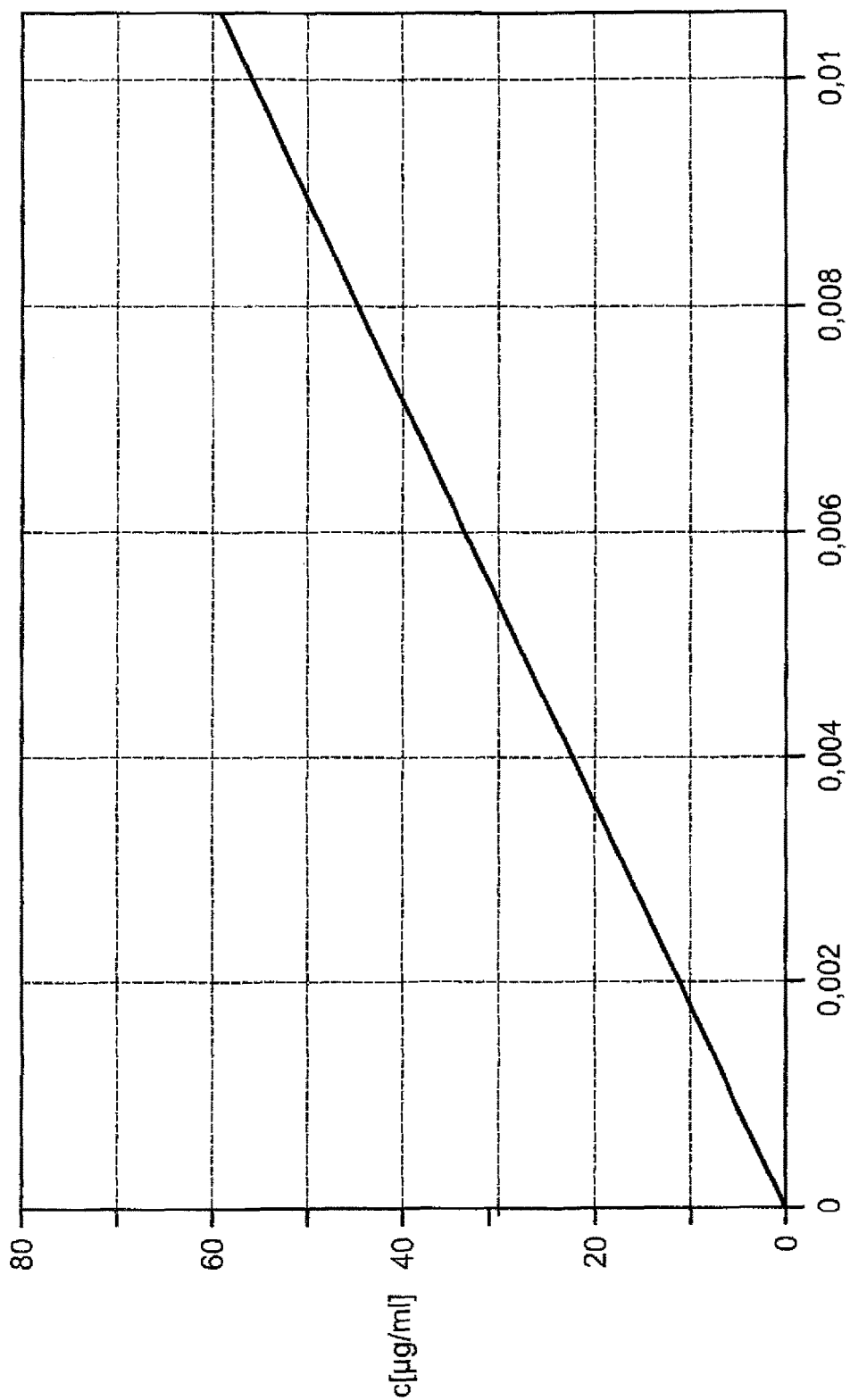
FIG. 2 shows a graphic representation of a calibration curve, wherein, on the base, the second derivative of the absorption and, on the ordinate, the concentration of glucoraphanin in an extract are indicated.

When the value of the minimum M has been determined, it is assigned a concentration value for the glucoraphanin concentration c of the diluted extract based on the calibration curve shown in FIG. 2. This value is 0.54 µg/ml. The concentration $y(1)$ of the glucoraphanin in the sample is determined as follows:

$$y(1) = a(1)\frac{m(\text{Extract, 1}) + m(\text{Methanol, 2})}{m(\text{Extract, 1})} \cdot \frac{m(\text{Methanol, 1})}{m(\text{Sample, 1})} = 163.45 \text{ mg}/100 \text{ g}$$

Herein are:
m(sample,1) the amount of the sample of the first attempt in [mg]
m(Methanol,1) the first amount methanol in [mg],
m(Methanol,2) the second amount methanol in [mg]
m(Extract,1) the amount of the undiluted extract of the first attempt in mg
c(1) the glucoraphanin concentration in the non-diluted extract of the first attempt,
y(1) the glucoraphanin concentration in the sample of the first attempt in [mg/100 g].

The calibration curve shown in FIG. 2 can be determined with the aid of examinations, wherein first a number of reference extracts which contain glucoraphanin in different concentrations are provided. The glucoraphanin concentrations of the reference extracts are preferably determined in such a way that the weight of a predetermined amount of glucoraphanin is determined and the amount is then dissolved in methanol. The weight of the methanol is also determined. The glucoraphanin concentration of the individual reference extracts corresponds then in each case to the quotient of the amount glucoraphanin and the sum of the glucoraphanin amount and the methanol amount.

For the reference extracts obtained in this way with the aid of the method according to the invention, in each case, the value of the minimum M of the second derivative of the absorption measurement signal in the second wavelength range is determined and is assigned to the concentration value of the respective reference extract.

The value combination obtained in this way which consist of the amount or value of the minimum M of the second derivative and the concentration value are recorded for example in a data storage device of a microcomputer as calibration values for determining the glucoraphanin concentration in future tests. The calibration curve can be provided in the form of a calculation instruction like for example a line equation or in the form of support points, which in each case, comprise the amount or the value of the minimum and a glucoraphanin concentration. Intermediate values between two support points may be interpolated when needed.

In an examination from the broccoli cress of the first try a second sample is provided which has a mass of 250 mg. The second sample is so comminuted that the glucoraphanin contained in the second sample comes into contact with the splitting enzyme so that sulforaphane is formed.

Now a predetermined time period has to be waited until the sulforaphane contained in the second sample is essentially completely evaporated. Then the second sample is mixed with a third amount of methanol of 1772 mg so that glucoraphanin which is still present in the second sample and which was not split into sulforaphane and the further plant material which is still contained in the second sample are dissolved in the methanol. From the extract obtained in this way undissolved plant parts are removed by filtration or centrifuging.

From the extract obtained thereby 18 mg are taken out and mixed with a second amount of methanol which has a mass of 728 mg, that is, the extract is diluted by the factor of 18/(18+728)=1:41.4. The dilution factor is determined based on the expectation value for the glucoraphanin concentration in such a way that, with a UV absorption measurement which is performed in a further method step which is to be described in greater detail, the absorption measuring apparatus is optimally adjusted if the concentration of glucoraphanin in the second sample after the evaporation of the sulforaphane coincides with the expectation values.

Now the already mentioned UV absorption measurement of the cleaned diluted extract which contains glucoraphanin and the additional plant material is performed in which, in the first wave length range, an absorption measuring signal is recorded.

If the measured absorption spectrum has in the first wavelength range measuring values above 2.5, it is assumed that the absorption measuring apparatus encountered saturation. In this case, the second attempt is interrupted and a new second test is performed in which a greater dilution factor is selected.

If the measured absorption spectrum in the first wave length range includes no measurement values above 2.5, the absorption measurement signal obtained in the second wavelength range is subjected to a double derivative.

In the second wavelength range, the value of the minimum of the second derivative of the absorption measurement signal in the area of the wavelength $\lambda_M$ of about 248 nm is determined. The value of the minimum is $5.29 \times 10^{-5}$.

To this value on the basis of the calibration curve shown in FIG. 2, a concentration value for the glucoraphanin concentration C of the diluted extract is assigned. This value is 0.31 µg/ml. The concentration y(2) of the glucoraphamine in the sample which during the comminution of the sample is not split into sulphoraphane is then as follows:

$$y(2) = c(2) \frac{m(\text{Extract, 2}) + m(\text{Methanol, 4})}{m(\text{Extract, 2})} \cdot \frac{m(\text{Methanol, 3})}{m(\text{Sample, 2})} = 91.07 \,\text{mg}/100 \,\text{g}$$

Herein are:
  m(Sample,2): the amount of the sample of the second attempt in [mg]
  m(Methanol,3): the third amount of methanol [mg]
  m(Methanol,4): the fourth amount of methanol [mg]
  m(Extract,2): the amount of the undiluted extract of the second attempt [mg]
  c(2): the glucoraphanin concentration in the diluted extract of the second attempt [µg/ml], and
  y(2): the concentration of the glucoraphamine in the sample which is not split during the comminution in [mg/100 g].

In a further method step, the concentration c(3) of the bio-available sulforaphane in the broccoli-cress is determined from the concentration value c(1) determined for the first sample and the concentration value c(2) determined for the second sample as follows:

$$C(3) = y(1) - y(2) = 72.38 \,\text{mg}/100 \,\text{g}.$$

What is claimed is:

1. A method for determining the concentration of glucoraphanin in a plant, comprising the steps:
  a) providing a sample of the plant,
  b) contacting the sample with a polar, uncharged organic solvent and comminuting the sample in such a way that glucoraphanin and further plant material contained in the sample are dissolved in the solvent thereby forming an extract,
  c) removing from the extract any undissolved plant components to clear the extract,
  d) performing a UV-absorption measurement of the cleared extract containing the glucoraphanin and the further plant material, wherein, for a first wavelength range of 200 nm to 270 nm, an absorption measurement signal is recorded,
  e) forming the second derivative of the absorption measurement signal for a second wavelength range of 240 nm to 250 nm, and
  f) determining a value of the minimum of the second derivative in the second wavelength range and, dependent on this value, determining a concentration value for the concentration of the glucoraphanin in the plant.

2. The method according to claim 1, wherein the absorption measurement signal is smoothness-filtered and the second derivative of the smoothness filtered absorption measurement signal is formed.

3. The method according to claim 1, wherein, in addition to the glucoraphanin, the plant contains spatially separated from the glucoraphanin, a splitting enzyme whereby, upon contact thereof with the glucoraphanin, sulforaphane is formed, the method comprising the steps of:
  a) with the sample of the plant provided determining a first concentration value for the concentration of the glucoraphanin in the first sample,
  b) providing a second sample of the plant, c) comminuting the second sample so that the glucoraphanin comes into contact with the splitting enzyme,
d) waiting for a predetermined period selected so as to permit the formation in the second sample of sulforaphane and the evaporation thereof,
e) contacting the second sample with a polar uncharged organic solvent so that glucoraphanin and further plant material contained in the second sample are dissolved in the solvent,
f) performing for the second sample the steps c) to f) of claim 1, and
g) determining as concentration value for the concentration of the bio-available sulforaphane of the plant the difference between the concentration value obtained for the first sample and the concentration value obtained for the second sample.

4. The method according to claim 1, wherein the absorption measurement signal determined in at least one of steps d) and f) of claim 1 is compared with a limit value and, in case the absorption measurement signal exceeds the limit value the extract is diluted in accordance with a dilution factor and step d) of claim 1 is repeated with the diluted extract, wherein the dilution factor is so selected that the absorption measurement signal of the diluted extract does not exceed the limit value, and then the steps e) and f) of claim 1 are performed with the absorption measurement signal obtained with the diluted extract and in accordance with step f) of claim 1 the concentration of the glucoraphanin in the plant is determined taking however the dilution factor into consideration.

5. The method according to claim 4, wherein the limit value is between 2 and 3.

6. A method for determining the concentration of bio-available sulphoraphane in a plant which contains glucoraphanin and spatially separated therefrom a splitting enzyme, wherein upon contact with the glucoraphanin of the plant sulforaphane is formed, the method comprising the steps of:
a) providing a first sample of the plant,
b) bringing the first sample in contact with a polar uncharged organic solvent and comminuting the first sample such that glucoraphanin and other plant material contained in the sample are dissolved in the solvent forming a first extract,
c) removing from the first extract undissolved plant parts to clear the first extract,
d) providing a second sample of the plant,
e) comminuting the second sample so that the glucoraphanin comes into contact with the splitting enzyme,
f) waiting for a predetermined period which is selected so as to permit the formation of sulforaphane in the second sample and the evaporation thereof,
g) contacting the second sample with a polar, uncharged organic solvent in such a way that glucoraphanin and further plant material contained in the second sample are dissolved in the solvent thereby forming a second extract,
h) removing undissolved plant components from the second extract to clear the second extract,
i) performing a first UV-absorption measurement of the cleared first extract which contains the glucoraphanin and the further plant material, whereby for the first wavelength range between 200 nm and 270 nm a first absorption measurement signal is recorded,
j) performing a second UV-absorption measurement of the cleared second extract which contains the glucoraphanin and the further plant material, whereby for the first wavelength range a second absorption measurement signal is recorded,
k) forming a differential signal from the first absorption measurement signal and the second measurement signal,
l) forming the second derivative of the differential signal for a second wavelength range of 240 nm to 250 nm, and
m) determining the value of the minimum of the second derivative of the differential signal obtained in the second wavelength range and, depending on this value, determining a concentration value for the concentration of the bio-available sulforaphane of the plant.

7. The method according to claim 6, wherein the absorptions measurement signal obtained in step i) of claim 6 is compared with a limit value, for the case that the absorption measurement signal exceeds the limit value, the extract is diluted according to a dilution factor, and the step i) of claim 6 is repeated with the diluted extract, the dilution factor being so selected that the absorption measurement signal of the diluted extract does not exceed the limit value and, using in step k) of claim 6 as first absorption measurement signal the absorption measurement signal of the diluted extract multiplied by the dilution factor.

8. The method according to claim 6, wherein at least one of the absorption measurement signal and the differential signal are smoothening-filtered and the second derivative is formed from the smoothening-filtered differential signal.

9. The method according to claim 1, wherein the plant is broccoli-cress.

10. The method according to claim 6, wherein the plant is broccoli-cress.

11. The method according to claim 1, wherein the solvent is methanol.

12. The method according to claim 6, wherein the solvent is methanol.

* * * * *